(12) United States Patent
Wahlström et al.

(10) Patent No.: US 11,952,323 B2
(45) Date of Patent: Apr. 9, 2024

(54) PROCESS AND APPARATUS FOR PRODUCING POLY-ALPHA-OLEFINS (71) Applicant: Neste Oyj, Espoo (FI)

(72) Inventors: Jan Wahlström, Porvoo (FI); Hanna Honkanen, Porvoo (FI); Veli-Matti Purola, Porvoo (FI); Filip Thierie, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 18/006,916

(22) PCT Filed: Jun. 14, 2022

(86) PCT No.: PCT/FI2022/050414
§ 371 (c)(1),
(2) Date: Jan. 26, 2023

(87) PCT Pub. No.: WO2022/263721
PCT Pub. Date: Dec. 22, 2022

(65) Prior Publication Data
US 2024/0034698 A1 Feb. 1, 2024

(30) Foreign Application Priority Data
Jun. 15, 2021 (FI) .................................. 20215704

(51) Int. Cl.
C07C 2/26 (2006.01)
B01J 3/00 (2006.01)
(Continued)

(52) U.S. Cl.
CPC ................ C07C 2/26 (2013.01); B01J 3/002 (2013.01); B01J 3/04 (2013.01); B01J 19/1881 (2013.01);
(Continued)

(58) Field of Classification Search
None
See application file for complete search history.

(56) References Cited

U.S. PATENT DOCUMENTS 4,045,508 A 8/1977 Cupples et al.
4,434,309 A 2/1984 Larkin et al.
(Continued)

FOREIGN PATENT DOCUMENTS

CA 2152669 A1 7/1994
CN 101490218 A 7/2009
(Continued)

OTHER PUBLICATIONS

Office Action dated Apr. 11, 2023, by the Canadian Patent Office in corresponding Canadian Patent Application No. 3,188,532. (7 pages).
(Continued)

Primary Examiner — Ali Z Fadhel
(74) Attorney, Agent, or Firm — BUCHANAN INGERSOLL & ROONEY PC (57) ABSTRACT The current disclosure relates to an apparatus and a process for producing poly-α-olefins (PAO), including reacting olefin monomers in a presence of a catalyst complex to form PAO product. The reaction is performed in a reaction including a reactor vessel and a system for recycling and cooling part of reactor outlet stream. At least one reactor is a cone reactor with a first cross sectional area in an upper part of the vessel and the cross sectional area decreases downwards to a second cross sectional area, which is smaller than the first cross sectional area.

17 Claims, 4 Drawing Sheets (51) Int. Cl.
  *B01J 3/04* (2006.01)
  *B01J 19/18* (2006.01)
  *B01J 27/12* (2006.01)
  *B01J 31/02* (2006.01)
(52) U.S. Cl.
  CPC ........... *B01J 27/12* (2013.01); *B01J 31/0202* (2013.01); *C07C 2531/22* (2013.01)

(56) References Cited

U.S. PATENT DOCUMENTS

| | | | |
|---|---|---|---|
| 4,870,143 A * | 9/1989 | Hashiguchi | B01J 8/20 526/236 |
| 5,877,375 A | 3/1999 | Clarembeau | |
| 6,147,271 A | 11/2000 | Strebel et al. | |
| 6,180,728 B1 | 1/2001 | Fanelli | |
| 10,822,435 B2 | 11/2020 | Banat | |
| 2006/0161034 A1 | 7/2006 | Surana et al. | |
| 2009/0076231 A1 * | 3/2009 | Broughton | C08F 2/16 526/64 |
| 2009/0221775 A1 | 9/2009 | Hagemeister et al. | |
| 2009/0281360 A1 | 11/2009 | Knowles et al. | |
| 2010/0081852 A1 | 4/2010 | Louret et al. | |
| 2012/0116141 A1 * | 5/2012 | Godsmark | C07C 2/12 585/533 |
| 2014/0058051 A1 * | 2/2014 | Weickert | B01J 8/1872 526/78 |
| 2014/0378720 A1 | 12/2014 | Wu et al. | |
| 2015/0166425 A1 | 6/2015 | Krupa et al. | |
| 2015/0232600 A1 * | 8/2015 | Keelapandal Ramamoorthy | C08F 2/01 422/134 |
| 2016/0002376 A1 * | 1/2016 | Kang | C08F 210/16 526/348.5 |
| 2017/0002113 A1 * | 1/2017 | Banat | B01J 8/0015 |
| 2018/0223020 A1 * | 8/2018 | Moorhouse | B01J 4/002 |
| 2018/0251582 A1 * | 9/2018 | Banat | C08F 10/02 |
| 2020/0087421 A1 * | 3/2020 | Banat | B01J 8/1836 |
| 2020/0255554 A1 * | 8/2020 | Banat | B01J 8/18 |
| 2020/0291143 A1 * | 9/2020 | Krallis | B01J 8/1827 |

FOREIGN PATENT DOCUMENTS

| | | |
|---|---|---|
| CN | 108350101 A | 7/2018 |
| CN | 111434753 A | 7/2020 |
| EP | 0493024 A2 | 7/1992 |
| WO | 2007144474 A1 | 12/2007 |
| WO | 2009097069 A1 | 8/2009 |

OTHER PUBLICATIONS

Search Report dated May 27, 2023, by the Chinese Patent Office in corresponding Chinese Application No. 202280005582.5. (3 pages).
Finnish Search Report issued in corresponding Patent Application No. 20215704 dated Nov. 1, 2021.
International Search Report (PCT/ISA/210) and Written Opinion (PCT/ISA/237) dated Sep. 23, 2022, by the European Patent Office as the International Searching Authority for International Application No. PCT/FI2022/050414.
Kenneth S. Whiteley, "Polyolefins" in Ullmann's Encyclopedia of Industrial Chemistry, Jan. 1, 2005, pp. 1-103.
Saptarshi Ray et al., "Poly-α-olefin-based synthetic lubricants: a short review on various synthetic routes", Lubrication Science, 2012 Sep. 5, 2011, vol. 24, 22 pages.
Office Action (Written Opinion and Search Report) dated Jun. 6, 2023, by the Singaporean Patent Office in corresponding Singaporean Patent Application No. 11202300851X. (9 pages).

* cited by examiner

PROCESS AND APPARATUS FOR PRODUCING POLY-ALPHA-OLEFINS

FIELD OF THE INVENTION

The present invention relates to a process and apparatus for producing poly-α-olefins (or poly-alpha-olefins; PAO) from α-olefin monomers. More particularly the invention relates to a process where PAO is produced in a reactor system with at least one reactor vessel with a cross sectional area, which decreases downwards to a smaller cross sectional area.

The present invention therefore provides a simplified and effective process and apparatus for production of PAO with high yields and effective use of raw material and catalyst material. The disclosed process also provides PAO products with optimized product distribution and composition.

BACKGROUND OF THE INVENTION

Oligomerisation reaction of α-olefins to form various grades of components useful in production of synthetic lubricants are well known. The production method generally includes oligomerisation of the α-olefin monomers using a catalyst or a catalyst complex, removal of the catalyst or catalyst complex from the reaction product and various post-reaction treatments of the oligomerisation product. The oligomerisation product is generally named poly-α-olefin (PAO) and can be categorised based on the viscosity as measured in cSt of the product. The viscosities of various PAO products can be e.g 2, 4, 6 or 8 cSt.

In the oligomerisation of α-olefins dimers, trimers, tetramers, pentamers etc. are formed. Heavier products, i.e. having a higher number of combined monomers in the oligomer, naturally have a higher viscosity compared to lighter products. PAO products are used in various applications and depending on the use, various viscosity and other properties are required of the PAO product. Different oligomers can also be combined to form products with desired properties.

Publication U.S. Pat. No. 4,434,309 describe oligomerisation of low molecular weight alpha olefins to produce synthetic lubricant base stock. The oligomerisation is performed in the presence of a catalyst, which can be boron trifluoride and a protonic promoter.

One key aspect of the production process is the separation of the catalyst or catalyst complex from the oligomerisation product. Publication EP 493 024 describes a typical PAO production process and separation of a catalyst complex containing boron trifluoride ($BF_3$) and butanol from the oligomerisation product with distillation under reduced pressure.

Key challenges in the PAO production process relate at least to the temperature control of the reaction, effective mixing of the catalyst with the monomer mixture to form a homogenous mixture ensuring effective reaction and control of the residence time to ensure optimal product distribution. The oligomerisation is an exothermic reaction and a set of process conditions needs to be controlled for reaction and product control and usage of monomers. The present invention provides a solution to these challenges.

BRIEF DESCRIPTION OF THE INVENTION

An object of the present invention is thus to provide a method and an apparatus for implementing the method so as to solve the above problems. The objects of the invention are achieved by a method and an apparatus which are characterized by what is stated in the independent claims. The preferred embodiments of the invention are disclosed in the dependent claims.

The invention thus provides a process for producing poly-α-olefins (PAO), the process comprising the following steps
 a) providing a reactor system comprising at least one reactor having a reactor vessel and a system for recycling and cooling part of reactor vessel outlet stream,
 b) introducing to at least one reactor vessel of the reactor system at least α-olefin monomers, recycled reactor outlet stream, catalyst and co-catalyst, which co-catalyst together with the catalyst forms a catalyst complex,
 c) reacting in the reactor vessel the α-olefin monomers to form a mixture of poly-α-olefins (PAO) product,
 d) withdrawing from the reactor vessel an outlet stream comprising unreacted monomers, mixture of PAO product and catalyst complex,
 e) splitting the outlet stream to a first stream, which is cooled and introduced back to the reactor vessel as a recycled reactor outlet stream, and a product stream, wherein
 at least one reactor in the reactor system is a cone reactor, in which cone reactor the reactor vessel has a first cross sectional area in an upper part of the vessel and the cross sectional area decreases downwards to a second cross sectional area, which is smaller than the first cross sectional area.

The current invention also provides an apparatus for performing the process according to the present invention, wherein the apparatus comprises a reactor system comprising at least one reactor having a reactor vessel and a system for recycling and cooling part of the reactor vessel outlet stream, means for introducing to at least one reactor vessel at least α-olefin monomers, recycled reactor outlet stream, catalyst and co-catalyst, and an outlet for withdrawing an outlet stream from the reactor vessel, wherein
 the at least one reactor vessel is a cone reactor, which cone reactor has a first cross sectional area in an upper part of the vessel and the cross sectional area decreases downwards to a second cross sectional area, which is smaller than the first cross sectional area.

BRIEF DESCRIPTION OF THE DRAWINGS

In the following the invention will be described in greater detail by means of preferred embodiments with reference to the figure, in which.

DETAILED DESCRIPTION OF THE INVENTION

The current invention relates to a process for producing poly-α-olefin (PAO), which is an oligomerisation product of α-olefins. The term "α-olefin" is here meant to denote the same as alpha-olefin, and is a 1-alkene, i.e. having a double bond in the primary carbon, also called a carbon. The carbon chain of the α-olefin is preferably linear, i.e. n-alkene. If not specifically mentioned that the α-olefin is branched, it is to be assumed that a linear α-olefin is meant. In one embodiment of the current invention the α-olefin monomer is $C_4$-$C_{20}$ α-olefins, preferably $C_8$-$C_{12}$ α-olefins and more preferably $C_{10}$ α-olefin (1-decene). It should be noted that even if the feedstock for the oligomerisation reaction comprises primary e.g. of C10-α-olefin (1-decene) the feedstock is never completely pure 1-decene and always contains various amounts of other olefins. The other olefins will also react in the oligomerisation reaction. Therefore, the PAO product formed in the oligomerisation reaction is always a mixture comprising products with different degree of oligomerisation (di-, tri, tetramers etc.) and oligomers from other olefin monomers than the primary chosen α-olefin of the feedstock.

The product of the oligomerisation reaction of the α-olefin monomers is named poly-α-olefin (PAO). The different oligomerisation products can be characterised based on the numbers of monomer-units in the oligomer, i.e. dimers, trimers, tetramers etc. The oligomerisation product can also be characterised based on the viscosity value as expressed in cSt of the product. Typical viscosities of light PAO products include but are not limited to 2, 4, 6, 8 etc kinematic viscosity at 100° C. in cSt.

A PAO product with a certain kinematic viscosity, such as 4 cSt or 6 cSt is most times a mixture of various oligomers. This is because the monomers containing feedstock is never completely pure and always contains a mixture of various α-olefins, but also because of various oligomers are always formed. However, it is not necessary to obtain pure products, i.e. products with only one type of oligomers, since it is the properties of the products which is significant, not the chemical structure. Products with specific properties, such as kinematic viscosities, are desired. Therefore, the product typically needs to be fractionated to obtain products with the desired properties. The oligomerisation reaction always provides a mixture of oligomers and the final PAO products are formed typically by fractionating the PAO reaction mixture to obtain products with desired properties, such as viscosity and volatility.

The oligomerisation reaction requires the use of a catalyst or catalyst complex. Typically, the oligomerisation is performed using a catalyst complex containing a catalyst and a co-catalyst. The term "catalyst complex" is here used to denote a combination of a catalyst and a co-catalyst (which can also be called a protonic promoter). The catalyst complex can be a physical mixture, or the catalyst and co-catalyst can be bounded with each other or it can be a combination of both. In one embodiment of the current invention the catalyst used in the oligomerisation of the α-olefin is aluminium halide or boron halide, boron trifluoride ($BF_3$) being a preferred catalyst. According to one embodiment the co-catalyst is selected from $C_1$-$C_{10}$ alcohol, preferably $C_1$-$C_5$ alcohol and most preferably n-butanol.

The performance and advantages of the current invention is not dependent on the chosen α-olefin or catalyst complex used in the oligomerisation. However, in one preferred embodiment of the invention the monomer is linear 1-decene and the catalyst complex is formed from $BF_3$ as catalyst with n-butanol as co-catalyst.

The process according to the invention involves providing a reactor system comprising at least one reactor having a reactor vessel and a system for recycling and cooling part of reactor vessel outlet. The term "reactor system" is here used to denote the system of one or more reactors where the oligomerisation reaction takes place. The term "reactor" or "PAO reactor" is here used to denote an individual reactor in the reactor system. The reactor contains a reactor vessel and a system for recycling and cooling part of reactor vessel outlet. The term "reactor vessel" is used to denote the vessel, where the oligomerisation reaction primarily takes place. The reactor, as denoted herein, also includes a system for recycling and cooling part of reactor vessel outlet stream.

The reactor vessel outlet stream is withdrawn from the reactor vessel, split into two separate streams. One of the outlet streams, which is splitted from the total outlet stream, is introduced to a system for recycling and cooling the stream. The cooling of the stream is performed in order to control the temperature of the reaction mixture. The oligomerisation reaction is an exothermic reaction and the temperature of the reaction mixture therefore increases over time, if not controlled. The cooled stream is re-introduced to the reaction vessel for further reaction.

According to the current invention the oligomerisation reaction is performed in a reactor system comprising at least one reactor, where the reactor contains a reactor vessel and a system for recycling and cooling part of reactor vessel outlet. According to the invention at least one reactor in the reactor system is a cone reactor, in which cone reactor the reactor vessel has a first cross sectional area in an upper part of the vessel and the cross sectional area decreases downwards to a second cross sectional area, which is smaller than the first cross sectional area.

The reactor system can contain more than one reactor. When the reactor system contains more than one reactor, at least one of the reactors in the reactor system is a cone reactor. In one embodiment of the current invention the reactor system contains one primary reactor, which is a cone reactor. If the reactor system contains one primary reactor, which is a cone reactor, the reactor system can in addition contain one or more secondary reactors, which can be but are not necessary cone reactors.

In one embodiment of the current invention the reactor system contains only one reactor, which is a cone reactor.

Figure 2A:
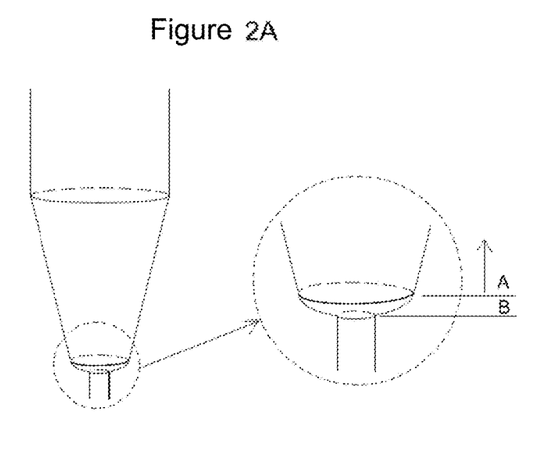

It should be noted that a reactor vessel can also comprise an outlet bottom section, which is rounded towards the bottom of the reactor vessel. The reactor vessel of the cone reactor, as used in the process according to the invention, has a reaction zone, depicted with A in FIG. 2A. The reactor may also have a rounded outlet zone, depicted with B in FIG. 2A. from which rounded outlet zone the reactor outlet stream is withdrawn. Where the reactor is a cone reactor, the reaction zone has a first cross sectional area in an upper part of the vessel and the cross sectional area decreases downwards to a second cross sectional area, which is smaller than the first cross sectional area.

Figure 2B:
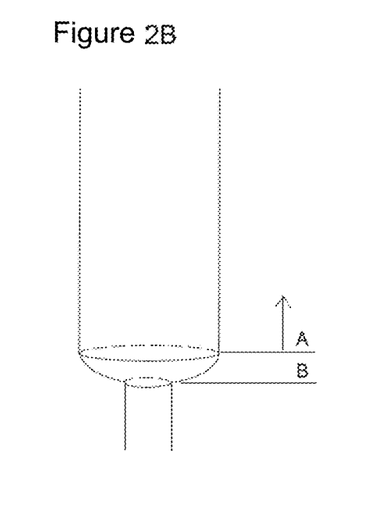

Also, cylindrical or tubular reactor vessels have a rounded outlet bottom section, depicted with B in FIG. 2B and a reaction zone, depicted with A in FIG. 2B. Therefore, the cone reactor in the process and apparatus according to the invention have a reaction zone (A) of the vessel, which have a first cross sectional area in an upper part of the vessel and the cross sectional area decreases downwards to a second cross sectional area, which is smaller than the first cross sectional area. The cylindrical or tubular reactor vessel of FIG. 2B is understood to have a reaction zone with only a cross sectional area essentially the same over the whole height of the reaction zone.

In one embodiment of the present invention the cone reaction has a reaction zone and the reactor outlet stream is withdrawn directly from the reaction zone, and the cone reactor does not have a rounded outlet zone. In a cone reactor without a rounded outlet zone the cone ends with a flange to the outlet piping, which forms the reactor outlet stream. The outlet piping needs to have a large diameter due to the large amount of cooling and recycling needed in the reactor.

It should be noted that a cylindrical or tubular reactor vessel almost always needs some sort of rounded or vertical outlet section to drive the reaction product towards the outlet piping. Also, the diameter of a cylindrical reactor is much greater than the diameter of the outlet piping.

In one embodiment of the invention the reaction zone of the cone reactor is divided to at least two sections, of which one section is a cone section, with a first cross sectional area in an upper part of the vessel and the cross sectional area decreases downwards to a second cross sectional area, which is smaller than the first cross sectional area. Thereby, also in a so called cone reactor the whole reactor vessel does not have to have a cone shape. Instead, a part of the reaction zone of the reactor vessel in a cone reactor can have a tubular shape and part can have a cone shape, where the cross sectional area decreases downwards in the reaction zone. The reaction zone of the cone reactor can have a length of between 0.2-10, preferably 0.3-8, more preferably 0.5-4, times the maximum diameter of the cone reactor at the site of the first cross sectional area.

In one embodiment of the present invention the reaction zone of the cone reactor has a tubular section, with a third cross sectional area in an upper part of the tubular section and a fourth cross sectional area at a lower part of the tubular section, which fourth cross sectional area is essentially equal to the third cross sectional area; and a cone section with a first cross sectional area in an upper part of the cone section and the cross sectional area decreases downwards to a second cross sectional area, which is smaller than the first cross sectional area. When the reaction has a tubular section and a cone section the length of the tubular section can be between 0.1-8, preferably 0.5-4, more preferably 1-3, times the diameter of cross sectional area of the tubular section, and the length of the cone section can be between 0.2-5, preferably 0.3-3, more preferably 0.5-1.5, times the maximum diameter of the cone section at the site of the first cross sectional area.

In one embodiment of the invention the volume of the cone section is between 0.1 and 5 times the volume of the system for recycling and cooling part of the reactor vessel outlet stream. Preferably the cone section volume is between 0.2 and 4, more preferably between 0.3 and 2, times the volume of the system for recycling and cooling part of the reactor vessel outlet stream.

In one embodiment the cone reactor has no external mixing or stirring device for mixing the reagents and catalyst complex. The cone shape of the reactor enables sufficient mixing of reagents and catalyst complex.

The residence time for the reaction mixture in the reactor, including reactor vessel and system for cooling and recycling part of the reactor vessel outlet stream, can be between 1 and 90 minutes, preferably between 3 and 60 minutes and more preferably between 5 and 40 minutes. The liquid residence time in the tubular section can be up to 5 times, preferably up to 4 and more preferably up to 2, times as compared to the liquid residence time in the cone section, when a reactor vessel with tubular and cone sections are used.

One objective of the current invention is therefore to provide a process for producing poly-α-olefins (PAO), the process comprising the following steps a) providing a reactor system comprising at least one reactor having a reactor vessel and a system for recycling and cooling part of the reactor vessel outlet stream, b) introducing to a at least one reactor vessel of the reactor system at least α-olefin monomers, recycled reactor outlet stream, catalyst and co-catalyst, which co-catalyst together with the catalyst forms a catalyst complex, c) reacting in the reactor vessel the α-olefin monomers to form a mixture of poly-α-olefins (PAO) product, d) withdrawing from the reactor vessel an outlet stream comprising unreacted monomers, mixture of PAO product and catalyst complex, e) splitting the outlet stream to a first stream, which is cooled and introduced back to the reactor vessel as a recycled reactor outlet stream, and a product stream, wherein at least one reactor in the reactor system is a cone reactor, which cone reactor has a first cross sectional area in an upper part of the vessel and the cross sectional area decreases downwards to a second cross sectional area, which is smaller than the first cross sectional area.

In one embodiment of the current invention the reactor system comprises more than one reactor. When more than one reactor in the reactor system, reactors can be in series, such that part of reactor vessel outlet stream is cooled and recycled back to same reactor vessel and part of outlet stream is introduced to the following reactor in the series. In the embodiment where the reactor system comprises more than one reactor, at least one of the reactors is a cone reactor.

The process according to the current invention comprises a step wherein an outlet stream comprising unreacted monomers, mixture of PAO product and catalyst complex is withdrawn from the reactor vessel. The withdrawn outlet stream is split into a first stream and a product stream (second stream). The first stream is cooled and introduced back to the reactor vessel as a recycled reactor outlet stream. The product stream split from the outlet stream constitutes the reaction product stream and is subjected to further processing step to produce the PAO product.

The separation of the outlet stream to two streams and subsequent cooling and recycling of the first stream is needed for controlling the temperature in the reactor. The oligomerisation reaction is exothermic and for optimal oligomer distribution, the conditions in the reactor should preferably be as isothermal or near isothermal as possible over the whole reactor. Cooling and recycling a portion of outlet stream withdrawn from the reactor vessel enables better control of the temperature conditions over the whole reactor. The aim is to achieve isothermal or near-isothermal conditions over the whole reactor including the cooling and recycling part of the outlet stream withdrawn from the reactor vessel.

In one embodiment of the current invention splitting of the outlet stream to a first stream and a product stream is performed such that 50-99%, preferably 80-97% and more preferably 90-95%, of the outlet stream forms the first stream and the rest forms the product stream. The portion of the first stream compared to the total reactor vessel outlet stream is large, more than 50% or even up to 99%. A large portion of recycling stream (first stream) ensures sufficient cooling of reaction mixture and thereby ensures iso-thermal or near isothermal conditions over the whole reactor.

A large portion of the reaction mixture, in an embodiment more than 50%, is in the reactor loop and not in the reactor vessel. This means half of the volume of reactor will be in turbulence in the recycle loop piping instead of being in a less turbulent reactor vessel, and all reaction mixture will go through the recycle loop frequently;

catalyst mixing at the reactor inlet will happen 10 times more than for a simple reactor without recycle loop; and reaction temperature during reaction will increase only by 10% compared to a once-through reactor vessel with cooling only at the outlet.

In one embodiment of the current invention introduction of the recycled reactor outlet stream to the reactor vessel is performed with an ejector. At least part of the catalyst can also be introduced to the reactor vessel using the ejector with which the recycled reactor outlet stream is introduced to the reactor vessel.

In one embodiment of the current invention the process further comprises a step f) wherein the product stream is subjected to a separation step for separating a PAO product stream from unreacted monomers and catalyst complex. It should be noted that the product stream is the stream which is split from the reactor outlet stream but not cooled and recycled back to the reactor vessel. Instead, the product stream is subjected to further process steps for production of the PAO product(s).

The separation of a PAO product stream from unreacted monomers and catalyst complex can be performed by distillation of the product stream. Unreacted monomers and catalyst complex have a lower boiling point compared to the product mixture of PAO and can therefore readily be separated by distillation. Also, other separation techniques can be used such as liquid-liquid separation or a combination thereof.

In one embodiment the separation of unreacted monomer and catalyst complex from the product mixture is performed using distillation in a temperature from 10° C. to 300° C., preferably from 20° C. to 150° C. in reduced pressure, where the pressure can be from 1 mbara to 20 mbara, preferably from 2 mbara to 10 mbara (0.1 kPa to 2 kPa, preferably 0.2 kPa to 1 kPa).

In one embodiment of the invention the method further comprises one or more addition steps in which the PAO product stream is further distilled into separate PAO fractions, e.g. based on the kinematic viscosity of the products. Either the PAO product stream as a whole or the PAO fractions after separation can also undergo a hydrogenation step. The hydrogenation step is preferably performed in presence of a noble metal or nickel catalyst, preferably a nickel catalyst. The hydrogenation can be performed in a fixed bed reactor.

Generally speaking, it is advantageous that the oligomerisation reaction results in a distinct product distribution, which can be separated into PAO fractions with distinct product properties, such as viscosity and volatility. Therefore, it is advantageous that the product distribution, regarding formed oligomers, is as narrow as possible. For example, it can be advantageous to obtain mainly trimers with less amounts of higher oligomers such as tetra- and pentamers. Another key issue is that the amounts of unreacted monomers should be as low as possible in the mixture of PAO product, i.e. a high yield. Various aspects and process conditions have a significant impact on which kind of oligomers are mainly formed.

The oligomers formed depend at least on the temperature in the reaction, residence time of the reagents in the reaction conditions and mixing of the catalyst complex in the monomers and product mixture. At least these conditions and aspects of the reaction need to be monitored and possible to control and alternate for optimal oligomer formation and overall results. With the current design of the reactor vessel with a narrower outlet part it is possible to control these process conditions. Especially compared to a reactor vessel with essentially equal cross sectional area over the whole reaction section, a reactor with narrower bottom section, the residence time can be controlled. The extensive recycling and cooling of the reaction mixture also enable improved control of the reaction temperature and in combination with the reactor vessel according to the invention it is possible to obtain isothermal reaction conditions over the whole reactor. The level formed from the reagents and catalyst complex (level of reagents) also varies more in different reactor capacities in a cone shaped reactor compared to a tubular shaped reactor. In connection with the reactor cone shape, functioning pump suction conditions, which includes required net positive suction head, can be maintained even at low reaction volume in the reactor vessel, because of the variation in level of reagents. This enables that the cooling recirculation can be kept at constant cooling duty, while enabling functioning pump suction conditions.

A product mixture containing a large number of unreacted monomers should be avoided. One way of avoiding unreacted monomers in the product mixture is to separate the unreacted monomers from the product mixture, e.g. by distilling. Another way is to ensure sufficient mixing of the catalyst complex into the feedstock and to maintain a homogeneous mixture also in the reaction product in the reactor. This is also enabled with the reactor vessel according to the invention.

Figure 1A:
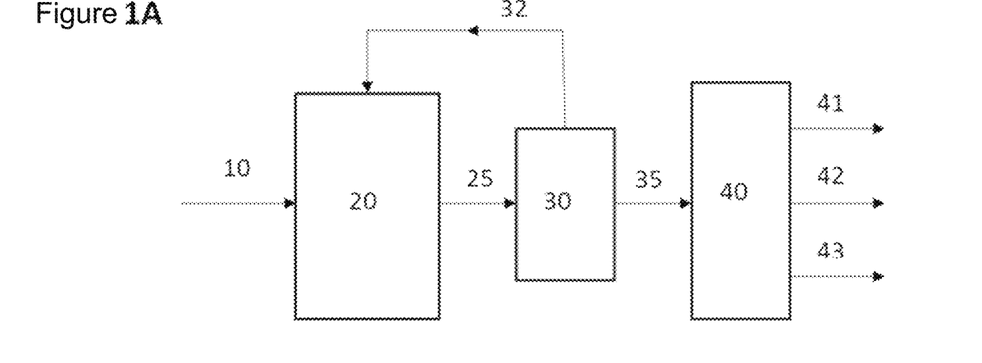
FIGS. 1A-1B are a schematic process description of the PAO process (FIG. 1A and a schematic process description of a reactor according to the invention (FIG. 1B), and
 FIGS. 2A-2B shows details of the reaction vessel used in the current invention, 2A and for comparison a cylindrical reaction vessel 2B.

FIG. 1A shows a schematic process of one embodiment of the current invention. A feedstock comprising at least α-olefin monomers and catalyst complex (10), which can be pre-mixed, is introduced to a PAO reactor system (20). The PAO reactor system can comprise one or more reactors. A reactor contains a reactor vessel and a system for recycling and cooling part of the reactor vessel outlet stream. At least one of reactors is a cone reactor with a reactor vessel which has a cone shape (not shown in FIG. 1A). In the PAO reactor system (20) the α-olefin monomers are oligomerized in presence of the catalyst complex and reaction product mixture comprising unreacted monomers, reaction product and catalyst complex is formed and removed as a product stream (25) from the PAO reactor system (20).

The product stream (25) removed from the PAO reactor system (20) is introduced to a separation unit (30) for separating at least unreacted monomers and catalyst complex from the PAO products. The separated unreacted monomer and catalyst complex stream (32) is recycled back to the PAO reactor system (20). The PAO product (35), from which at least unreacted monomers and catalyst complex (stream 32) are removed, is withdrawn from the separation unit (30) for further treatment (40). The further treatment can comprise at least separation of various PAO products to separate PAO fractions (41, 42 and 43). The schematic FIG. 1A shows formation of three PAO fractions, but this should be interpreted only as an example and the fractions can be more than three or less than three. The PAO fractions (41, 42 and 43) can be subjected as separate fractions to hydrogenation, or alternatively the PAO product (35) can be hydrogenated before separation to PAO fractions. The separation of the PAO product (35) to PAO fractions (41, 42 and 43) is typically performed by distillation.

Figure 1B:
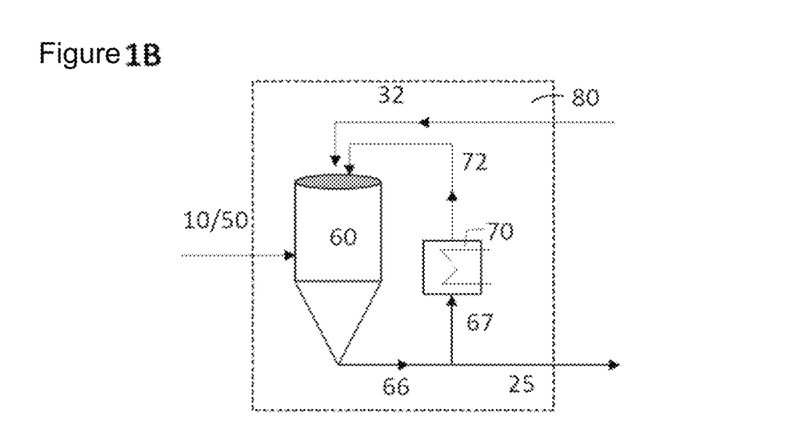

FIG. 1B shows a schematic process of a PAO reactor (80) comprising a PAO reactor vessel (60) and a system for cooling and recycling part of the reactor vessel outlet (70 and streams 67 and 72). A fresh feedstock comprising α-olefin monomers and catalyst complex (10) or a reaction mixture from a reactor upstream (50) is introduced to the PAO reactor vessel (60). A reactor vessel outlet stream (66) is withdrawn from the reactor vessel (60) and split to two streams. A first stream (67) is directed to a heat exchanger (70) for cooling. The cooled recycled stream (72) is directed back to the reactor vessel (60) for further reaction. Part of the reactor vessel outlet stream (66) is split to a product stream (25). This product stream (25) contains PAO product mixture, unreacted monomers and catalyst complex. This product stream (25) is directed to the separation unit (30) depicted in FIG. 1A. FIG. 1B also shows the stream (32) from the separation unit (30), which contains the separated unreacted monomers and catalyst complex. This stream is depicted as one stream in FIGS. 1A and 1B but can also be two or more separate streams, some stream(s) containing the unreacted monomers and other stream(s) containing the catalyst complex and/or catalyst.

Figure 3A:
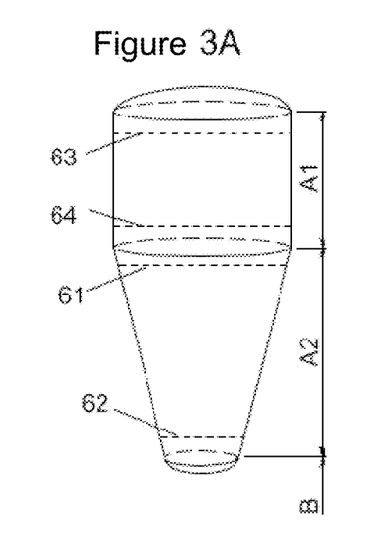
FIGS. 3A-3C shows details of various reactor shapes used in the current invention, 3A and 3B and for comparison a cylindrical reaction vessel 3C.
Figure 3B:
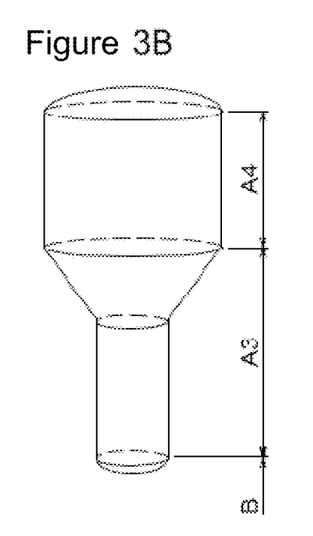
Figure 3C:
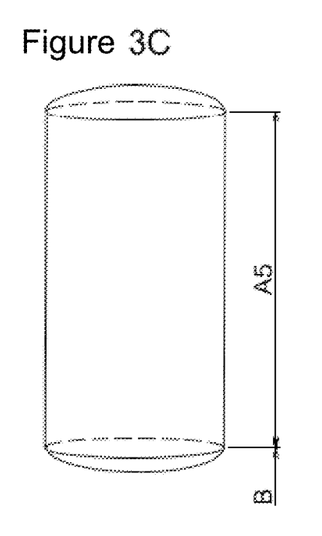

FIGS. 3A-3C shows two different reactors with a shape according to the current invention, 3A and 3B, as well as a cylindrical reactor, 3C, for comparison. Reactor shape 3A is according to the invention and in the figure a rounded outlet zone B is shown, and a reaction zone, A1 and A2. According to the present invention the reactor vessel with a cone shape can have a rounded outlet zone, but not necessary. The reaction zone is separated in two sections, a cone section A2 and a tubular section A1. The cone section A1 has a first cross sectional area (61) and a second cross sectional area (62). The second cross sectional area (62) is smaller than the first cross sectional area (61). The tubular section A1 has a third cross sectional area (63) and a fourth cross sectional area (64). The third cross sectional area (63) is essentially equal to the fourth cross sectional area (64).

FIG. 3B shows a reactor shape according to the invention having a reaction zone A3 and A4 and a rounded outlet zone B. The reaction zone in FIG. 3B is separated to two sections, a cone section A3 and a tubular section A4. For comparison, in FIG. 3C a tubular reactor is shown with a reaction zone A5 and a rounded outlet zone B. The reaction zone A5 of the cylindrical reactor (3C) cannot be separated into reaction sections.

The current invention also relates to an apparatus for performing the process according to the invention, wherein the apparatus comprises a reactor system comprising at least one reactor having a reactor vessel and a system for recycling and cooling part of the reactor vessel outlet stream, means for introducing to at least one reactor vessel at least α-olefin monomers, recycled reactor outlet stream, catalyst and co-catalyst, and an outlet for withdrawing an outlet stream from the reactor vessel, wherein at least one reactor vessel is a cone reactor, which cone reactor has a first cross sectional area in an upper part of the vessel and the cross sectional area decreases downwards to a second cross sectional area, which is smaller than the first cross sectional area.

The disclosed apparatus can further comprise means for splitting the outlet stream to a first stream and a product stream; and means for cooling the first stream and recycling the first stream to the reactor vessel.

It will be obvious to a person skilled in the art that, as the technology advances, the inventive concept can be implemented in various ways. The invention and its embodiments are not limited to the examples described above but may vary within the scope of the claims.

EXAMPLES

Oligomerisation of 1-decene was tested in a 0.002 m$^3$ batch reactor. The reaction was catalysed with a 1 mol-% of boron trifluoride (BF3) n-butanol complex. The pressure in the reactor was set at 200 kPa and controlled with a flow of BF3 gas. The temperature was controlled with a cooling jacket and an internal coil. The batch reactor was mixed with a turbine mixer. Mixing was necessary since the batch-reactor did not contain any recycling, which would enable sufficient mixing. The products were analysed using gas chromatography and a mass spectrometer detector.

Example 1

First a series of reactions were conducted to test the speed of reaction (oligomerisation) in various temperatures. Three different reaction temperatures were chosen, 10° C., 30° C. and 70° C. The reactions were performed in isothermal conditions, as set out above. The reaction speed was determined as the speed of which the monomer 1-decene was decreased in the reaction mixture.

The conversion rate, indicated as decrease of monomer 1-decene, of the reaction at various temperatures can be seen in Table 1 below.

TABLE 1

Conversion rate as a function of reaction temperature. A conversion of 100% indicates that all monomers (1-decene) have been consumed.

| Reaction temperature | Conversion % | | | | |
|---|---|---|---|---|---|
| | 5 min | 10 min | 20 min | 30 min | 60 min |
| 10° C. | 30 | 43 | 65 | 75 | 100 |
| 30° C. | 50 | 70 | 90 | 97 | 100 |
| 70° C. | 60 | 85 | 90 | 93 | 100 |

From the results shown in Table 1, it can be seen that at a reaction temperature of 10° C. the reaction was significantly slower compared to higher temperatures of 30° C. and 70° C. Full conversion at 10° C. was reached after about 60 min reaction time. The results also show that increasing the temperature from 30° C. to 70° C. did not significantly increase the conversion rate. Full conversion was in practice reached at 30 min reaction time, when the reaction temperature was 30° C. and 70° C.

Example 2

A reaction temperature of 30° C. was chosen as the optimal reaction temperature, based on the findings from Example 1. A set of reactions were performed using the same equipment and parameters as in Example 1. Here the product distribution was measured as a function of reaction time. The total reaction time was 120 min.

The oligomerisation of 1-decene and formation of trimers and tetramers is shown in Table 2 below.

TABLE 2

Results of oligomerization reaction in laboratory batch reactor
Oligomerisation of 1-decene

| Residence time min | Trimer wt-% | Tetramer wt-% | Trimer selectivity % | Tetramer selectivity % |
|---|---|---|---|---|
| 0 | 0 | 0 | 0 | 0 |
| 5 | 30 | 9 | 59 | 18 |
| 10 | 39 | 15 | 55 | 22 |
| 20 | 47 | 26 | 50 | 28 |
| 30 | 46 | 27 | 46 | 28 |

TABLE 2-continued

Results of oligomerization reaction in laboratory batch reactor
Oligomerisation of 1-decene

| Residence time min | Trimer wt-% | Tetramer wt-% | Trimer selectivity % | Tetramer selectivity % |
|---|---|---|---|---|
| 60 | 46 | 29 | 46 | 29 |
| 90 | 43 | 29 | 43 | 30 |
| 120 | 44 | 30 | 44 | 30 |

The results summarized in the Table 2 indicate that trimer selectivity can be maximized with a short residence time. A long residence time yields heavier oligomers. Based on the results, it is evident that the residence time influences the product formation. Therefore, reaction residence time and critical operation condition parameters should be kept unchanged during operation to optimize product selectivity, even at various capacities.

Example 3

Previous examples show the significance of reaction temperature, but especially residence time, to obtain optimal product distribution. Calculations were made using a cone shape reactor to optimise residence time with different capacities of the reactor. In the calculations a 100% capacity was set at 13 125 kg/h. The volume of the cooling loop, pump and piping was fixed. In the simulations 100% capacity was set such, that the level of reagents was at the top of the inverted cone reactor, cone section A2. Calculations were made with 100%, 90%, 80%, 70% and 60% reactor capacity. The results of the calculations are summarised in Table 3.

TABLE 3

Residence time optimisation in cone reactor with various capacities.

| | Capacity | | | | |
|---|---|---|---|---|---|
| | 60% | 70% | 80% | 90% | 100% |
| Cone | | | | | |
| Level of Reagents [m] | 0.41 | 0.89 | 1.16 | 1.36 | 1.52 |
| Volume [m3] | 0.08 | 0.36 | 0.64 | 0.92 | 1.2 |
| Residence time [min] | 0.5 | 1.9 | 2.9 | 3.7 | 4.3 |
| Loop | | | | | |
| Volume [m3] | 1.59 | 1.59 | 1.59 | 1.59 | 1.59 |
| Residence time [min] | 9.5 | 8.1 | 7.1 | 6.3 | 5.7 |
| Cone + Loop | | | | | |
| Volume [m3] | 1.68 | 1.96 | 2.24 | 2.52 | 2.8 |
| Residence time [min] | 10 | 10 | 10 | 10 | 10 |
| Loop Circulation system | | | | | |
| Cone avg. suction velocity [m/s] | 0.32 | 0.33 | 0.36 | 0.40 | 0.44 |
| Loop Pump [m3/h] | 180 | 210 | 240 | 270 | 300 |

From the results of table 3 it can be seen that the total residence time can be kept at 10 min at various reactor capacities. The volume of the loop (meaning cooling loop, pump and piping) is constant at 1.59 m³. The level of reagents in the cone section of the reactor is varied with the capacities. By varying the loop circulation pump velocity (from 180 m³/h to 300 m³/h) the cooling recirculation can be kept at constant cooling duty for all capacities while, in connection with the reactor cone shape, functioning pump suction conditions including required net positive suction head can be maintained even at low reaction volume in the reactor vessel.

Figure 4:
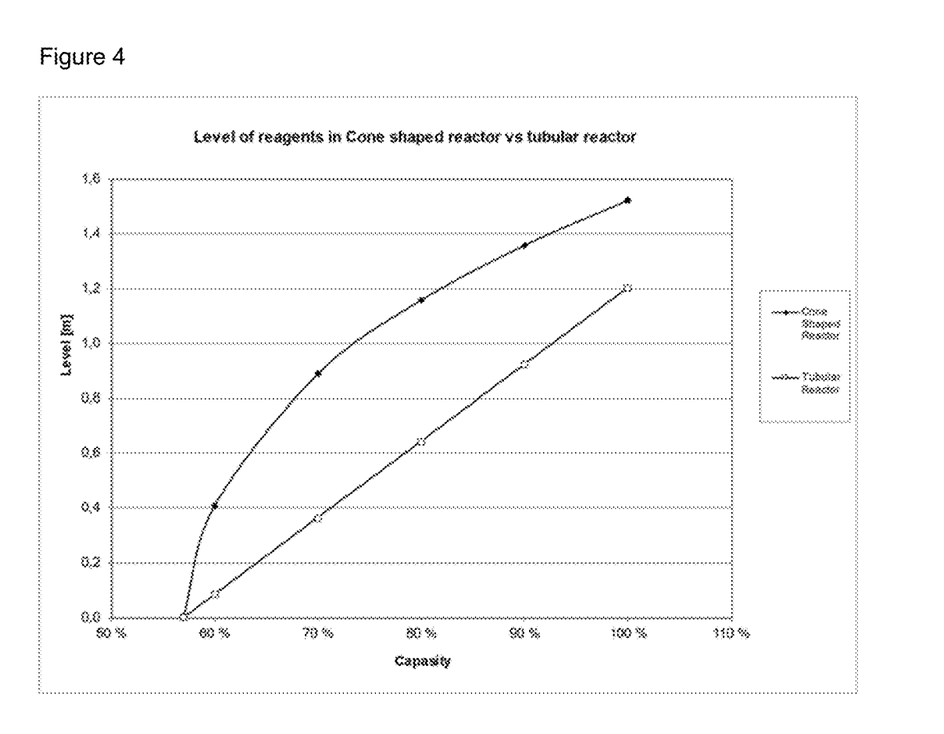
FIG. 4 shows level of reagents in cone shaped reactor versus tubular shaped reactor at various capacities.

FIG. 4 shows the difference in level of reagents in a cone reactor and in a tubular reactor at various reactor capacities. From FIG. 4 it can be seen that the level decreases faster at lower capacities in a cone shaped reactor compared to a tubular shaped reactor. It is therefore easier to monitor variations in the level of reagents in a cone reactor compared to a tubular shaped reactor, especially in lower reactor capacities.

The invention claimed is:

1. A process for producing poly-α-olefins (PAO), the process comprising:
   a) providing a reactor system including at least one reactor having a reactor vessel and a system for recycling and cooling part of reactor vessel outlet stream;
   b) introducing to at least one reactor vessel of the reactor system at least α-olefin monomers, recycled reactor outlet stream, catalyst and co-catalyst, which co-catalyst together with the catalyst forms a catalyst complex;
   c) reacting in the reactor vessel the α-olefin monomers to form a mixture of poly-α-olefins (PAO) product;
   d) withdrawing from the reactor vessel an outlet stream including unreacted monomers, the mixture of PAO product and the catalyst complex; and
   e) splitting the outlet stream to a first stream, which is cooled and introduced back to the reactor vessel as a recycled reactor outlet stream, and a product stream; wherein
   at least one reactor in the reactor system is a cone reactor, in which cone reactor the reactor vessel has a first cross sectional area in an upper part of the vessel the cross sectional area decreases downwards to a second cross sectional area, which is smaller than the first cross sectional area.

2. The process of claim 1, wherein the cone reactor has a reaction zone and a rounded outlet zone from which the reactor outlet stream is withdrawn, and wherein the reaction zone has a first cross sectional area in an upper part of the vessel and the cross sectional area decreases downwards to a second cross sectional area, which is smaller than the first cross sectional area.

3. The process of claim 1, wherein the cone reactor has a reaction zone and the reactor outlet stream is withdrawn directly from the reaction zone, and the cone reactor does not have a rounded outlet zone.

4. The process of claim 2, wherein the reaction zone of the cone reactor is divided to at least two sections, of which one section is a cone section, with a first cross sectional area in an upper part of the vessel and the cross sectional area decreases downwards to a second cross sectional area, which is smaller than the first cross sectional area.

5. The process of claim 1, wherein a reaction zone of the cone reactor has a length of between 0.2-5, and/or 0.3-3, and/or 0.5-1.5, times a maximum diameter of the cone reactor at a site of the first cross sectional area.

6. The process of claim 4, wherein the reaction zone of the cone reactor has a tubular section, with a third cross sectional area in an upper part of the tubular section and a fourth cross sectional area at a lower part of the tubular section, which fourth cross sectional area is essentially equal to the third cross sectional area; and wherein a cone section has the first cross sectional area in an upper part of the cone section and the cross sectional area decreases downwards to the second cross sectional area, which is smaller than the first cross sectional area.

7. The process of claim 6, wherein a length of the tubular section is between 0.1-8, and/or 0.5-4, and/or 1-3, times a diameter of cross sectional area of the tubular section, and a length of the cone section is between 0.2-5, and/or 0.3-3, and/or 0.5-1.5, times a maximum diameter of the cone section at a site of the first cross sectional area.

8. The process of claim 1, wherein the introducing of the recycled reactor outlet stream to the reactor vessel is performed with an ejector.

9. The process of claim 8, wherein at least part of the catalyst is introduced to the reactor vessel using the ejector with which the recycled reactor outlet stream is introduced to the reactor vessel.

10. The process of claim 1, wherein the α-olefin monomer comprises:
$C_4$-$C_{20}$ α-olefins, and/or $C_8$-$C_{12}$ α-olefins and/or $C_{10}$ α-olefin.

11. The process of claim 1, wherein the catalyst is an aluminium halide or a boron halide, and/or the catalyst is $BF_3$ and the co-catalyst is selected from $C_1$-$C_{10}$ alcohols, and/or the co-catalyst is n-butanol.

12. The process of claim 1, wherein the splitting of the outlet stream to a first stream and a product stream is performed such that 50-99%, and/or 80-97% and/or 90-95%, of the outlet stream forms the first stream and a remainder forms the product stream.

13. The process of claim 1, comprising:
step f) wherein the product stream is subjected to a separation step for separating a PAO product stream from unreacted monomers and catalyst complex.

14. The process of claim 13, wherein the step f) is performed by distillation in a temperature of 10° C. to 300° C. in reduced pressure, and the separation step also separates the catalyst complex, as catalyst and co-catalyst, from the unreacted monomers.

15. The process according to claim 13, wherein the PAO product is processed by separating the PAO product in further PAO fractions followed by hydrogenation of the PAO fractions in a presence of a noble metal catalyst or nickel catalyst, or hydrogenation of the PAO product in a presence of a noble metal catalyst or nickel catalyst followed by separation of the hydrogenated PAO product in further hydrogenated PAO fractions.

16. An apparatus for performing a process for for producing poly-α-olefins (PAO), which includes:
a) providing a reactor system including at least one reactor having a reactor vessel and a system for recycling and cooling part of reactor vessel outlet stream;
and co-catalyst, which co-catalyst together with the catalyst forms a catalyst complex: catalyst b) introducing to at least one reactor vessel of the reactor system at least α-olefin monomers, recycled reactor outlet stream,
c) reacting in the reactor vessel the α-olefin monomers to form a mixture of poly-α-olefins (PAO) product;
d) withdrawing from the reactor vessel an outlet stream including unreacted monomers, the mixture of PAO product and the catalyst complex; and
e) splitting the outlet stream to a first stream, which is cooled and introduced back to the reactor vessel as a recycled reactor outlet stream, and a product stream; wherein
at least one reactor in the reactor system is a cone reactor, in which cone reactor the reactor vessel has a first cross sectional area in an upper part of the vessel the cross sectional area decreases downwards to a second cross sectional area, which is smaller than the first cross sectional area, wherein the apparatus comprises;
a reactor system including at least one reactor having a reactor vessel and a system for recycling and cooling part of reactor vessel outlet stream;
means for introducing to at least one reactor vessel at least α-olefin monomers, recycled reactor outlet stream, catalyst and co-catalyst; and
an outlet for withdrawing an outlet stream from the reactor vessel, wherein:
the at least one reactor vessel is a cone reactor, which cone reactor has a first cross sectional area in an upper part of the vessel and the cross sectional area decreases downwards to a second cross sectional area, which is smaller than the first cross sectional area.

17. The apparatus of claim 16, wherein the apparatus comprises:
means for splitting the outlet stream to a first stream and a product stream; and
means for cooling the first stream and recycling the first stream to the reactor vessel.

* * * * *